United States Patent
Tomokuni et al.

(10) Patent No.: US 9,072,674 B2
(45) Date of Patent: Jul. 7, 2015

(54) SKIN CLEANSING AGENT COMPOSITION

(75) Inventors: Atsushi Tomokuni, Shinagawa-ku (JP); Tomonori Fukuchi, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/130,792

(22) PCT Filed: Jul. 3, 2012

(86) PCT No.: PCT/JP2012/004311
§ 371 (c)(1),
(2), (4) Date: Jan. 3, 2014

(87) PCT Pub. No.: WO2013/005422
PCT Pub. Date: Jan. 10, 2013

(65) Prior Publication Data
US 2014/0142016 A1     May 22, 2014

(30) Foreign Application Priority Data

Jul. 4, 2011 (JP) .................................. 2011-148707

(51) Int. Cl.
| | |
|---|---|
| C11D 1/66 | (2006.01) |
| C11D 1/825 | (2006.01) |
| C11D 3/18 | (2006.01) |
| A61K 8/34 | (2006.01) |
| A61Q 1/14 | (2006.01) |
| A61K 8/37 | (2006.01) |
| A61K 8/86 | (2006.01) |
| A61Q 19/10 | (2006.01) |
| A61K 8/81 | (2006.01) |

(52) U.S. Cl.
CPC ... *A61K 8/37* (2013.01); *A61Q 1/14* (2013.01); *A61K 8/86* (2013.01); *A61Q 19/10* (2013.01); *A61K 8/345* (2013.01); *A61K 8/8158* (2013.01); *A61K 8/8182* (2013.01); *A61K 8/34* (2013.01); *A61K 8/8147* (2013.01)

(58) Field of Classification Search
CPC ............ C11D 1/66; C11D 1/825; C11D 3/18; C11D 3/2006; C11D 3/2041; C11D 3/2065; C11D 3/3757; A61K 8/34; A61Q 1/14
USPC ......... 510/136, 147, 153, 155, 159, 421, 437, 510/475; 424/70.11, 70.15, 70.16, 70.19, 424/70.31
See application file for complete search history.

(56) References Cited

U.S. PATENT DOCUMENTS

| | | |
|---|---|---|
| 2004/0136943 A1 | 7/2004 | Tomokuni |
| 2005/0180942 A1 | 8/2005 | Shimizu et al. |
| 2008/0182771 A1 | 7/2008 | Murase et al. |
| 2008/0188395 A1 | 8/2008 | Murase et al. |
| 2012/0073591 A1* | 3/2012 | Chen ............................ 132/200 |

FOREIGN PATENT DOCUMENTS

| | | | |
|---|---|---|---|
| CN | 101234070 A | 8/2008 | |
| JP | 2004 002292 | 1/2004 | |
| JP | 2004 026791 | 1/2004 | |
| JP | 2004 075566 | 3/2004 | |
| JP | 2004 217640 | 8/2004 | |
| JP | 2004 238376 | 8/2004 | |
| JP | 2007 320884 | 12/2007 | |
| JP | 2008 184413 | 8/2008 | |
| JP | 2008 184414 | 8/2008 | |
| JP | 2008 184415 | 8/2008 | |
| JP | 2008 266224 | 11/2008 | |
| JP | 2010 280597 | 12/2010 | |
| JP | 2011 012057 | 1/2011 | |
| JP | 2011 012252 | 1/2011 | |
| WO | WO 2010/140319 | * 12/2010 | ............... A61K 8/81 |
| WO | WO 2010/140329 A1 | 12/2010 | |

OTHER PUBLICATIONS

International Search Report Issued Oct. 16, 2012 in PCT/JP12/004311 Filed Jul. 3, 2012.
Combined Chinese Office Action and Search Report issued Dec. 31, 2014 in Patent Application No. 201280033401.6 (with English language translation of Office Action and English translation of categories of cited documents).

* cited by examiner

*Primary Examiner* — Brian P Mruk
(74) *Attorney, Agent, or Firm* — Oblon, McClelland, Maier & Neustadt, L.L.P.

(57) ABSTRACT

A skin cleansing agent composition of the present invention contains an isotropic liquid phase, which is a bicontinuous structure, and containing: 15 to 30 mass % of a nonionic surfactant having HLB of higher than 9 and equal to or lower than 20; 1 to 15 mass % of a nonionic surfactant having HLB of equal to or higher than 5 and equal to or lower than 9; 10 to 40 mass % of an oil agent exhibiting a viscosity at 30 degrees C. of equal to or lower than 30 mPa·s; 10 to 40 mass % of a water-soluble solvent having 3 or more of hydroxyl groups in single molecule; 10 to 30 mass % of a water-soluble solvent having 1 or 2 hydroxyl group(s) in single molecule; 0.05 to 1.0 mass % of a water-soluble polymer containing (meta) acrylic acid as a configuration unit and/or an acryloyl methyl taurate-vinylpyrrolidone copolymer; 0.001 to 2.0 mass % of a water-soluble inorganic salt and/or an organic salt having 1 to 8 carbon atoms; and water.

26 Claims, No Drawings

SKIN CLEANSING AGENT COMPOSITION

TECHNICAL FIELD

The present invention relates to a skin cleansing agent composition.

BACKGROUND ART

In recent years, various types of skin cleansing agent compositions are developed according to diversification of makeup cosmetic compositions and needs of consumers. For example, cleansing cosmetic compositions as described in Patent Documents 1 to 4, which are usable for skins wetted with water, are known.

Also, Patent Document 5 describes a skin cleansing agent composition, which contains a lipid component, a hydrophilic nonionic surfactant, a lipophilic amphipathic substance, a water-soluble solvent and water at specific ratio, and also contains bicontinuous structure having isotropic liquid phase.

Also, Patent Documents 6 to 8 describe a cleansing composition having enhanced cleansing-ability for waterproof type mascara.

Also, Patent Document 9 describes an O/W-type emulsion cleansing agent composition, which exhibits enhanced effect for dissolving severe solid stains formed in pores of skin, in particular in keratotic plugs, to achieve improved effect for eliminating the keratotic plugs.

Also, Patent Document 10 describes that a liquid skin cleansing agent with enhanced cleansing-ability, which involves improved massaging ability and persistent massaging ability, is obtained by combining a specific water-soluble polymer (carboxy vinyl polymer or alkyl-modified carboxy vinyl polymer and salt thereof) dissolved in an aqueous solvent with a liquid water-soluble salt and an oil agent.

RELATED DOCUMENTS

Patent Documents

[Patent Document 1] Japanese Laid-Open Patent Application Publication No. 2004-26791
[Patent Document 2] Japanese Laid-Open Patent Application Publication No. 2004-2292
[Patent Document 3] Japanese Laid-Open Patent Application Publication No. 2004-75566
[Patent Document 4] Japanese Laid-Open Patent Application Publication No. 2004-238376
[Patent Document 5] Japanese Laid-Open Patent Application Publication No. 2004-217640
[Patent Document 6] Japanese Laid-Open Patent Application Publication No. 2008-184413
[Patent Document 7] Japanese Laid-Open Patent Application Publication No. 2008-184414
[Patent Document 8] Japanese Laid-Open Patent Application Publication No. 2008-184415
[Patent Document 9] Japanese Laid-Open Patent Application Publication No. 2011-12252
[Patent Document 10] Japanese Laid-Open Patent Application Publication No. 2010-280597

SUMMARY OF INVENTION

The present invention is to provide a skin cleansing agent composition having an isotropic liquid phase, which is a bicontinuous structure, and containing the following components (A), (B), (C), (D), (E), (F), (G), and (H):

(A) 15 to 30 mass % of a nonionic surfactant having hydrophilic-lipophilic balance (HLB) of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water.

DESCRIPTION OF EMBODIMENTS

There is still a need to be improved in the technologies described in the above-described Documents on the cleansing of the makeup cosmetic composition such as waterproof type mascara and the like, which is hard to be removed.

The technologies described in Patent Documents 1 to 4 employ continuous phase of the cleansing agents (outer phase) composed of oil, and thus it feels oily in the rinsing, and oiliness feel easily remains after the rinsing.

Since the cleansing agent having the bicontinuous structure as described in Patent Document 5 is capable of creating the continuous phase in either oil phase or water phase, such cleansing agent exhibits higher cleansing-ability for both of the powder stain such as foundation and the like and the water-soluble stain, and such cleansing agent can be clearly rinsed off without an oiliness feel for the oily stain having higher water resistance and oil resistance such as waterproof type mascara and the like, which cannot be easily removed by particularly employing a conventional cleansing agent. Also, the cleansing agents described in Patent Documents 6 to 8 exhibit higher cleansing-ability, and can be clearly rinsed off.

However, the skin cleansing compositions described in Patent Documents 5 to 8 exhibit very low viscosities and thus are easily dripped down, and therefore there is a problem that it is difficult to apply such compositions sufficiently over the skin. Thus, the cleansing-ability which the cleansing agent having the bicontinuous structure originally has cannot be sufficiently exhibited on the skin.

It is considered that a water-soluble polymer is added over the technologies described in Patent Documents 5 to 8 in order to increase the viscosity. However, since the bicontinuous structure is created under the delicate balances of the components, O/W-type emulsion is generated by merely adding a water-soluble polymer as described in Patent Document 9, and therefore a stable bicontinuous structure as a product cannot be formed.

The skin cleansing agent described in Patent Document 10 contains smaller amount of surfactants, and this Document does not disclose a cleansing agent having bicontinuous structure.

The present invention is directed to obtaining a cleansing agent having a stable bicontinuous structure and exhibiting enhanced application-ability and spreading-ability over the skin, in which phase is not changed even if water is mixed to maintain enhanced cleansing-ability.

The inventors of the present application have found that a skin cleansing agent composition containing bicontinuous structure, which involves enhanced stability and improved application-ability to the skin, can be obtained by blending specific amounts of a specific polymer and a specific water-soluble salt in a formulation containing specific amounts of specific types of nonionic surfactant, oil agent, and water-soluble solvent, which are blended in water. Further, the inventors of the present application have also found that even a certain amount of mixed water causes no change of the phase in such skin cleansing agent composition and still maintains enhanced spreading-ability.

The skin cleansing agent composition of the present invention has stable bicontinuous structure and moreover has enhanced application-ability and enhanced spreading-ability over the skin, and even a certain amount of mixed water causes no change of the phase, and both of higher cleansing-ability and improved rinsing-ability can be achieved.

The nonionic surfactant of component (A) employed in the present invention has hydrophilic-lipophilic balance (HLB) of higher than 9 and equal to or lower than 20. In the present specification, hydrophilic-lipophilic balance (HLB: balance between hydrophilicity and lipophilicity) represents molecular weight of hydrophilic group segment in the whole molecular weight of the surfactant, and HLB for the nonionic surfactant is obtained by equation of Griffin's method shown below.

$$HLB=E/5$$

E: percentage presented by mass of the polyoxyethylene segment contained in the surfactant molecule.

The nonionic surfactant of the component (A) employed in the present invention is not particularly limited to any specific surfactant, as long as HLB is higher than 9 and equal to or lower than 20, preferably HLB is equal to or higher than 10 and equal to or lower than 17, and typical nonionic surfactant is, for example, composed of fatty ester having 8 to 22 carbon atoms, or ether of higher alcohol having 8 to 22 carbon atoms, which has hydroxyl group and/or ethylene oxide group as hydrophilic functional group.

Specific compounds for the component (A) includes: fatty acid polyglycerides; polyethylene glycol fatty acid esters; polyoxyethylene glycerol fatty acid esters; propylene glycol fatty acid esters; polyoxyethylene polyoxypropylene glycol esters; sorbitan fatty acid esters; polyoxyethylene sorbitan fatty acid esters; polyoxyethylene sorbitol fatty acid esters; polyoxyethylene castor oil; polyoxyethylene hydrogenated castor oil; polyoxyethylene hydrogenated castor oil fatty acid esters; polyalkyl glyceryl ethers; polyoxyethylene alkyl ethers; polyoxyethylene alkyl ether fatty acid esters; saccharose fatty acid esters; alkyl polyglucosides; alkyl glyceryl ethers and the like. Among these, in view of cleansing-ability, fatty acid polyglycerides; polyethylene glycol fatty acid esters; polyoxyethylene glycerol fatty acid esters; polyoxyethylene sorbitol fatty acid esters; alkyl glyceryl ethers; polyoxyethylene alkyl ethers; saccharose fatty acid esters and alkylpoly glucosides are advantageous. In view of the cleansing-ability for the oily stains, polyethylene glycol fatty acid ester, polyoxyethylene glycerol fatty acid ester, polyoxyethylene sorbitol fatty acid ester and alkylpoly glucoside are even more preferable.

One or more of compound(s) may be employed for the component (A), and from the viewpoint of providing the stability of the bicontinuous structure, it is preferable to employ a combination of two to five compounds. More specifically, it is preferable to employ a combination of a surfactant having linear alkyl chain and a surfactant having alkyl group having branch or unsaturated group. Also, it is preferable to employ a combination of a surfactant having only polyoxyethylene chain in the hydrophilic group and a surfactant having glycerol and sugar skeleton. Specifically, it is preferable to contain a polyethylene glycol fatty acid ester and one or more selected from a polyoxyethylene glycerol fatty acid ester, a polyoxyethylene sorbitol fatty acid ester and an alkylpoly glucoside. Further, in view of providing improved stability at the lower temperature, it is preferable to employ a combination containing a polyoxyethylene glycerol fatty acid ester and a polyethylene glycol fatty acid ester, and it is even more preferable to employ a combination containing all of a polyethylene glycol fatty acid ester, a polyoxyethylene glycerol fatty acid ester, a polyoxyethylene sorbitol fatty acid ester and an alkylpoly glucoside.

The content of the component (A) is 15 to 30 mass % in the skin cleansing agent composition of the present invention. This allows the agent being clearly rinsed away without a remaining feel. Further, it is more preferable to contain this at 17 to 20 mass % in the skin cleansing agent composition of the present invention. The content within this range provides improved compatibility with the makeup and is capable of floating the stain, and moreover can be clearly rinsed off without a pasty feel and without a remaining feel.

From the viewpoint that the cleansing agent forms the bicontinuous structure, the component (A) may be configured that the content of a silicone based surfactant in the skin cleansing agent composition is preferably equal to or lower than 1 mass %, and more preferably equal to or lower than 0.1 mass %, and it even more preferably contains no silicone based surfactant.

The nonionic surfactant of component (B) employed in the present invention has HLB of equal to or higher than 5 and equal to or lower than 9. HLB is obtained by equation of Griffin's method shown below, as described above. It is preferable that HLB of the component (B) is equal to or higher than 5 and equal to or lower than 8, in relation to creating the bicontinuous structure by combining with the component (A). Specific compounds for the component (B) include: fatty acid polyglycerides such as diglyceryl oleate, diglyceryl isostearate and the like; polyglycerol alkylethers such as diglycerol 2-ethylhexyl ether, isostearyl glyceryl ether and the like; polyethylene glycol fatty acid esters such as polyethylene glycol (5) monostearic acid ester and the like. In view of creating the bicontinuous structure to achieve improved stability, the component (B) preferably contains a surfactant having alkyl group having branch or unsaturated group, and more specifically diglyceryl oleate, diglyceryl isostearate and isostearyl glyceryl ether are even more preferable. In addition to above, from the viewpoint that the cleansing agent forms the bicontinuous structure, the component (B) may be configured that the content of a silicone based surfactant in the skin cleansing agent composition is preferably equal to or lower than 1 mass %, and more preferably equal to or lower than 0.1 mass %, and it even more preferably contains no silicone based surfactant.

One or more of compound(s) may be employed for the component (B). The content of the component (B) is 1 to 15 mass % in the skin cleansing agent composition of the present invention, and in view of achieving sufficient cleansing-ability, 2 to 10 mass % is preferable, and further, 2.5 to 5 mass % is more preferable.

Mass ratio of the component (B) over the total mass of the component (A) and the component (B) in the skin cleansing agent composition of the present invention: ((B)/((A)+(B))) is preferably 0.05 to 0.21, and is more preferably 0.1 to 0.2 in view of the stability of the bicontinuous structure for the temperature. It is preferable to set the lower limit of equal to or higher than 0.10, in view of the improvement in the stability for the high temperature.

The component (C) employed in the present invention is an oil agent composed of: (C1) hydrocarbon oils; and one, two or more compound(s) selected from the group consisting of (C2) ester oils and (C3) ether oils, in which the viscosity at 30 degrees C. is equal to or lower than 30 mPa·s. Here, the viscosity of the component (C) is to be measured by employing BM type viscometer (commercially available from TOKIMEC Co., Ltd., measurement conditions: rotor No. 1, 60 rpm, for one minute). Such oil agent of lower viscosity exhibits higher permeability to micro segments and higher solubility for the stains, so that enhanced cleansing-ability is achieved for oily makeup stains such as an oily mascara and the like. Further, such oil agent does not involve strong oily feel, and exhibits improved feel of use. It is preferable that the component (C) is liquid at 20 degrees C., since this provides enhanced cleansing-ability for the reason described above.

Liquid oils, which are ordinarily employed for cosmetic compositions and satisfy the above-described conditions, may be employed for such oil agent. For example, liquid paraffin, liquid isoparaffin, scualane, isododecane and the like may be employed for the hydrocarbon oil of the component (C1). Among these, liquid isoparaffin, especially hydrogenated polyisobutene is preferable. It is preferable to employ the compound having the polymerization degree of isobutene of 3 to 6, in view of the cleansing-ability characteristics for the oily stain.

Also, specific compounds available for ester oils of the component (C2) include, for example: isostearic acid cholesteryl ester (cholesteryl isostearate); isopropyl palmitate; isopropyl myristate; isopropyl isostearate; octadecyl myristate; cetyl 2-ethylhexanoate; isononyl isononanoate; isotridecyl isononanoate; neopentylglycol dicaprate; glyceryl tri(2-ethylhexanoate); glyceryl tri(caprylate/caprate) and the like. In view of difficulty in precipitation of crystal, ester oils having branched alkyl chain is even more preferable.

Also, specific compounds available for ether oils of the component (C3) include ether oils such as alkyl-1,3-dimethylbutyl ether, dioctyl ether, nonylphenyl ether and the like.

Among these, the oil agent having molecular weight of equal to or lower than 300 is preferable for the oil agent of the component (C) in view of the cleansing-ability. The compounds corresponded to the above includes, more specifically: isoparaffins such as liquid isoparaffin, light liquid isoparaffin, hydrogenated poly isobutene and the like as the component (C1); isopropyl myristate, isopropyl palmitate and isononyl isononanoate as the component (C2); and dioctyl ether and the like as the component (C3). Further, in view of the rinsing-ability, the combination of the component (C1) and the component (C2) is preferable, and the combination of isoparaffin, especially a liquid isoparaffin, and isopropyl myristate is preferably employed.

The content of the oil agent of the component (C) is 10 to 40 mass % in the skin cleansing agent composition of the present invention, and is even more preferably 15 to 30 mass %, allowing the agent being clearly rinsed away without a remaining feel while maintaining sufficient cleansing-ability.

The oil agent of component (C) is configured that mass ratio of the component (C1) over the total mass of the ester oil of the component (C2) and the ether oil of the component (C3) in the skin cleansing agent composition of the present invention: ((C1)/((C2)+(C3))) is preferably equal to or higher than 0.3 and is more preferably equal to or higher than 0.5, and on the other hand is preferably equal to or lower than 3 and is more preferably equal to or lower than 2, and is also preferably 0.3 to 3 and, in view of the temperature stability, is more preferably 0.5 to 2. It is even more preferable from the viewpoint of the temperature stability to contain isopropyl myristate at equal to or higher than 5 mass % in the whole component (C).

Mass ratio of the component (C) over the mass of the component (A) in the skin cleansing agent composition of the present invention: ((C)/(A)) is preferably 0.5 to 2, and is preferably 0.5 to 1.5, and is more preferably 0.8 to 1.2, which allows the agent being clearly rinsed away without a remaining feel while maintaining sufficient cleansing-ability.

The water-soluble solvent of the component (D) is a compound having three or more hydroxyl group in molecule. More specifically, this includes: glycerols such as glycerol, diglycerol and the like; saccharides such as sorbitol, maltitol, maltose, fructose, xylitol, maltotriose, threitol, erythritol, glucose and the like; and sugar derivatives such as methylglucoside, ethylglucoside and the like. The component (D) functions as a solvent for obtaining the bicontinuous structure of the present invention. Among these, glycerol, sorbitol and maltitol are even more preferable, since the bicontinuous structure can be maintained to enhance the moisture retention effect even if a larger amount thereof is contained. Further, glycerol and sorbitol are preferable in view of the rinsing-ability.

One or more of compound(s) may be employed for the component (D), and it is preferable to employ a combination of two or more compounds.

The component (D) is contained at 10 to 40 mass % in the skin cleansing agent composition of the present invention, and even more preferably is contained at 21 to 30 mass %, which allows the agent being clearly rinsed away without a remaining feel while exhibiting sufficient cleansing-ability.

The water-soluble solvent of the component (E) is a compound having one or two hydroxyl group in molecule. More specifically, this includes, for example: monatomic alcohols such as ethanol, propanol, isopropanol, butanol, isobutanol and the like; and glycols such as ethylene glycol, propylene glycol, diethylene glycol, dipropylene glycol, 1,3-butylene glycol, 1,4-butylene glycol, hexylene glycol, isoprene glycol and the like. The component (E) functions as a solvent for obtaining the bicontinuous structure of the present invention. Among these, compounds having two hydroxyl groups in molecule is preferable, and 1,3-butylene glycol, isoprene glycol, propylene glycol and dipropyleneglycol are even more preferable, in view of the temperature stability from the low temperature to the high temperature.

One or more of compound(s) may be employed for the component (E). The content of the component (E) is equal to or higher than 10 mass % in the skin cleansing agent composition of the present invention, and is preferably equal to or higher than 11 mass %, and on the other hand equal to or lower than 30 mass %, and is preferably equal to or lower than 20 mass % and is more preferably equal to or lower than 15 mass %, and is 10 to 30 mass %, and is preferably 11 to 15 mass % to provide the stability over the wider range of the temperature and achieve the clear rinsing ability without a remaining feel.

Mass ratio of the component (D) over the component (E) in the skin cleansing agent composition of the present invention: ((D)/(E)) is preferably 0.1 to 2.5, and is more preferably 1 to 2.5. The component (D) serves as enhancing superficial hydrophobicity in the whole skin cleansing agent composition. Thus, this configuration is preferable in view of adjusting the balance for maintaining the bicontinuous structure when water is mixed.

The component (F) employed in the present invention is composed of one, two or more of component(s) selected from water-soluble polymers containing (meth)acrylic acid as structural unit (water-soluble polymers containing structural unit derived from (meth)acrylic acid) and acryloyl methyl taurate-vinylpyrrolidone copolymers. The component (F) serves as increasing the viscosity of the skin cleansing agent composition of the present invention such that the drip of the liquid is avoided when this is coated over the skin, and this can be sufficiently mixed with the stains such to provide easy cleansing.

The water-soluble polymer which contains structural unit of (meth)acrylic acid is a compound synthesized by employing (meth)acrylic acid as monomer, and is typically, for example, an acrylic acid-alkyl methacrylate copolymer, which is typically a cross linking-type copolymer of acrylic acid and alkyl (C10 to C30) methacrylate, and more typically the commercially available products of, for example, PEMULEN TR-1, PEMULEN TR-2, PEMULEN TR-1, PEMULEN TR-1, Carbopol ETD 2020 (commercially available from Lubrizol Advanced Materials Inc.) and the like.

The water-soluble polymer containing (meth)acrylic acid of the component (F) as the structural unit is preferably employed by neutralizing all of or a portion of the unit of (meth)acrylic acid with an alkali agent. The alkali agent for the neutralization is not particularly limited as long as the agent is the alkali agent that can be ordinarily blended in the cosmetic compositions, and for example, potassium hydroxide, sodium hydroxide and the like may be employed. One of, or a combination of two or more of, compound(s) may be employed for the alkali agent, and it is preferable to contain the agent at equal to or higher than 0.01 mass % and equal to or lower than 1.0 mass % in the skin cleansing agent composition of the present invention to provide the adjusted pH at 5.5 to 9, more preferably at 6 to 8.

The acryloyl methyl taurate vinylpyrrolidone copolymer of the component (F) may be commercially available products of, for example, acryloyl dimethyl taurine ammonium/VP copolymer, Aristoflex AVC (commercially available from Clariant Inc.). The acryloyl methyl taurate vinylpyrrolidone copolymer may be preferably contained at equal to or higher than 0.01 mass % and equal to or lower than 1.0 mass % in the skin cleansing agent composition of the present invention to preferably provide the adjusted pH at 4 to 9, more preferably at 5 to 7.

One of, or a combination of two or more of, a water-soluble polymer containing acrylic acid as the structural unit of monomer or an acryloyl methyl taurate vinylpyrrolidone copolymer may be employed for the component (F).

In addition to above, the alkyl methacrylate copolymer acrylate is even more preferable for the component (F), since this configuration provides easy spreading over the skin when the cleansing agent is spread over the skin to apply the cleansing agent to the stains, according to the mutual action with a component (G) as will be discussed later to generate an elasticity vertically to the direction of spreading.

One or more of the compounds may be employed for the component (F), and in view of providing controlled liquid characteristics of the cleansing composition, the component (F) is contained at 0.05 to 1.0 mass %, preferably at 0.05 to 0.8 mass %, and more preferably contained at 0.1 to 0.5 mass %.

Mass ratio of the component (F) over the total mass of the component (A) and the component (B) in the skin cleansing agent composition of the present invention: ((F)/((A)+(B))) is preferably 0.001 to 0.06, and more preferably with the lower limit of equal to or higher than 0.003 in view of the stability of the temperature stability, and with the upper limit of equal to or lower than 0.045 in view of the rinsing-ability.

The component employed in the present invention (G) is composed of one, two or more of components selected from water-soluble inorganic salts and organic salts having 1 to 8 carbon atoms. The water solubility used here is determined as a compound, equal to or larger than 5 g of which can be dissolved in 100 g of water at 20 degrees C. The water-soluble salt of the component (G) is hydrated and dissolved, and thus superficial hydrophobicity of the whole skin cleansing agent composition is enhanced. Thus, the balance for maintaining the bicontinuous structure can be adjusted when water is mixed. Also, this serves as reducing the influence of the component (F) on the bicontinuous structure.

Specifically, the water-soluble inorganic salts typically include metallic hydroxide of alkali metals and salts of ammonium with hydrochloric acid, sulfuric acid, nitric acid, phosphoric acid, triphosphoric acid, pyrophosphoric acid and carbonic acid, and more specifically include: chlorides such as sodium chloride, potassium chloride, magnesium chloride and the like; sulfates such as sodium sulfate, potassium sulfate, magnesium sulfate, aluminum sulfate and the like; and carbonates such as sodium carbonate, sodium hydrogen carbonate and the like.

The water-soluble organic salts having 1 to 8 carbon atoms typically include salts of acids such as lactic acid, succinic acid, citric acid, tartaric acid, malic acid, maleic acid, fumaric acid and the like with alkali metal, ammonium and the like, and typically include: monosodium citrate, disodium citrate, trisodium citrate, potassium lactate, ammonium succinate, potassium malate and the like. The compound having 6 or less carbon atoms is more preferable, and it is also preferable to contain none of amino acids and compounds that are capable of creating inner salt.

Among these, in view of the stability, sodium chloride and potassium chloride are preferable for the water-soluble inorganic salt, and salts of polyhydric acids having hydroxyl group with alkali metals are preferable for the water-soluble organic salts having 1 to 8 carbon atoms, and salts of citric acid, tartaric acid and malic acid with sodium and potassium are more preferable. In view of providing improved liquid characteristics of the skin cleansing agent composition, it is even more preferable to employ an inorganic salt as the component (G).

One or more of the water-soluble salt(s) may be employed for the component (G), and in view of adjusting the balance for creating the bicontinuous structure of the skin cleansing agent composition of the present invention to maintain such structure even in the case of being mixed with water, this is contained at 0.001 to 2.0 mass % in the skin cleansing agent composition of the present invention, and is preferably contained at 0.005 to 1.0 mass %, and more preferably at 0.01 to 1.0 mass %.

Mass ratio of the component (F) over the component (G): ((F)/(G)) is preferably 0.1 to 10, more preferably 1 to 7, and further preferably 2 to 7. The ratio within this range allows the water-soluble polymer of component (F) being shrunk in the composition by the presence of the component (G), so that elasticity is vertically generated when the cleansing agent is applied and spread, allowing considerably easy spreading. Also, the concentration of the component (G) in the composition is diluted with a slight amount of water entered from wet hand or skin so that the water-soluble polymer of component (F) is spread to exhibit thickener function. Consequently, even if the hand or the skin is wet in the use, the composition can be employed without problem without considerable decrease in the viscosity of the composition. In view of maintaining the liquid characteristics including enhanced spreading-ability in the application of the composition when water is mixed therein, the ratio is preferably 2 to 7. The lower limit is determined to be equal to or higher than 2 to provide the skin cleansing agent with further enhanced spreading-ability. On the other hand, the upper limit is determined to be equal to or lower than 7 to provide the skin cleansing agent with enhanced application-ability.

Water of the component (H) is contained in the skin cleansing agent composition of the present invention at preferably equal to or higher than 5 mass %, at more preferably equal to or higher than 10 mass %, and on the other hand at preferably equal to or lower than 50 mass %, at more preferably equal to or lower than 40 mass %, and further preferably equal to or lower than 30 mass %, and is also contained therein at preferably 5 to 50 mass %, at more preferably 10 to 40 mass %, and further preferably at 10 to 30 mass %, in view of being clearly rinsed without remaining feel while maintaining sufficient cleansing-ability.

Also, it is preferable to contain the components (D), (E) and (H) at a total amount of 40 to 80 mass % and even more preferable 45 to 70 mass % in the skin cleansing agent composition of the present invention, since this achieves both sufficient cleansing-ability and clear rinsing.

The skin cleansing agent composition of the present invention may further contain an oil agent except the component (C). More specifically: methylcyclo polysiloxanes such as decamethyl cyclopenta siloxane, octamethylcyclotetra siloxane and the like; silicone oils such as methyl polysiloxane, methylphenyl polysiloxane and the like; and animal and vegetable oils such as olive oil and the like may be contained. Nevertheless, it is preferable to contain such oil agent as long as the bicontinuous structure composed of the above-described components (A) to (F) is not broken.

In addition to above, when a combination of two or more of the oil agents except the component (C) is employed, one or more of the oil agent(s) having the viscosity in 30 degrees C. of larger than 30 mPa·s may be employed, and in such case, two or more oil agents are suitably selected for the combination so as to provide the viscosity of the oil agent composition mixed with the oil agent of the component (C) of equal to or lower than 30 mPa·s at 30 degrees C.

The skin cleansing agent composition of the present invention may further contain, in addition to the components (A) to (G), components that are ordinarily employed for the cleansing agent, typically for example, thickening agents, disinfecting agents, moisturizing agents, humectants, colorants, antiseptic agents, feel improvers, odorants, anti-inflammatory agents, skin-lightening agents, antiperspirants, UV absorbers, antioxidants, various types of extracts and the like, may be suitably contained. In this regard, in view of obtaining the stable bicontinuous structure over the temperature, an ionic surfactant is preferably contained in the skin cleansing agent composition of the present invention at equal to or lower than 0.5 mass %, and is contained further preferably at equal to or lower than 0.05 mass %, and none of the ionic surfactant is more preferably contained.

The skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water,
in which the mass ratio of the aforementioned component (B) over the total mass of the aforementioned component (A) and the aforementioned component (B) being $((B)/((A)+(B)))$ is 0.05 to 0.21, and is preferably 0.1 to 0.2.

Alternatively, the skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water,
in which the mass ratio of the component (F) over the total mass of the component (A) and the component (B) being $((F)/((A)+(B)))$ is 0.001 to 0.06, and is preferably 0.003 to 0.045.

Alternatively, the skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meta)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water, in which the mass ratio of the component (D) over the component (E) being ((D)/(E)) is 0.1 to 2.5.

Alternatively, the skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water,
in which the mass ratio of the aforementioned component (F) over the aforementioned component (G) being ((F)/(G)) is 0.1 to 10, preferably 1 to 7, and further preferably 2 to 7.

Alternatively, the skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water,
in which the mass ratio of the aforementioned component (C1) over the total mass of the aforementioned component (C2) and the aforementioned component (C3) being ((C1)/((C2)+(C3))) is 0.3 to 3, and is also preferably 0.5 to 2.

Alternatively, the skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20;
(B) 1 to 15 mass % of a nonionic surfactant having HLB of equal to or higher than 5 and equal to or lower than 9;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water,
in which the mass ratio of the aforementioned component (C) over the mass of the aforementioned component (A) being ((C)/(A)) is 0.5 to 2, and is preferably 0.5 to 1.5.

The skin cleansing agent composition of the present invention may be a skin cleansing agent composition having an isotropic liquid phase, which is a bicontinuous structure, and containing:
(A) 15 to 30 mass % of a nonionic surfactant having HLB of higher than 9 and equal to or lower than 20, and preferably a nonionic surfactant having HLB of equal to or higher than 10 and equal to or lower than 17, more preferably containing a combination of two or more of nonionic surfactants, in which a combination of a surfactant having linear alkyl chain and a surfactant having alkyl group having branch or unsaturated group is preferably employed and a combination of a surfactant having only polyoxyethylene chain in the hydrophilic group and a surfactant having glycerol and sugar skeleton is employed;
(B) 1 to 15 mass % of a nonionic surfactant having HLB of equal to or higher than 5 and equal to or lower than 9, and preferably having HLB of equal to or higher than 5 and equal to or lower than 8;
(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s, and preferably (C1) the hydrocarbon oil is a liquid isoparaffin and (C2) the ester oil is a ester oil having branched alkyl chain;
(D) 10 to 40 mass % of a water-soluble solvent having 3 or more of hydroxyl groups in single molecule;
(E) 10 to 30 mass % of a water-soluble solvent having 1 or 2 hydroxyl group(s) in single molecule;
(F) 0.05 to 1.0 mass % of a water-soluble polymer containing (meth)acrylic acid as a configuration unit and/or an acryloyl methyl taurate-vinylpyrrolidone copolymer;
(G) 0.001 to 2.0 mass % of a water-soluble inorganic salt and/or an organic salt having 1 to 8 carbon atoms; and
(H) water.

Alternatively, in the skin cleansing agent composition of the present invention, the content of the component (A) is 15 to 30 mass % in the whole formulations, and further, more preferably 17 to 20 mass %.

The content of the component (B) is 1 to 15 mass % in the whole formulations, and preferably 2 to 10 mass %, and further, more preferably 2.5 to 5 mass %.

The content of the component (C) is 10 to 40 mass % in the whole formulations, and further, more preferably 15 to 30 mass %.

The content of the component (D) is 10 to 40 mass % in the whole formulations, and further, more preferably 21 to 30 mass %.

The content of the component (E) is 10 to 30 mass % in the whole formulations, and further, more preferably 11 to 15 mass %.

The content of the component (F) is 0.05 to 1.0 mass % in the whole formulations, and preferably 0.05 to 0.8 mass %, and further, more preferably 0.1 to 0.5 mass %.

The content of the component (G) is 0.001 to 2.0 mass % in the whole formulations, and preferably 0.005 to 1.0 mass %, and further, more preferably 0.01 to 1.0 mass %.

The content of the component (H) is 5 to 50 mass % in the whole formulations, and more preferably 10 to 40 mass %, and further preferably 10 to 30 mass %.

The skin cleansing agent composition of the present invention may be a skin cleansing agent composition having an isotropic liquid phase, which is a bicontinuous structure, and containing:
(A) 17 to 20 mass % of a nonionic surfactant having hydrophilic-lipophilic balance (HLB) of equal to or higher than 9 and equal to or lower than 20;
(B) 2.5 to 5 mass % of a nonionic surfactant having HLB of equal to or higher than 5 and equal to or lower than 9;
(C) 15 to 30 mass % of and oil agent, which is composed of (C1) a hydrocarbon oil, (C2) ester oil and/or (C3) an ether oil and exhibits a viscosity at 30 degrees C. of equal to or lower than 30 mPa·s;
(D) 21 to 30 mass % of a water-soluble solvent having 3 or more of hydroxyl groups in single molecule;
(E) 11 to 15 mass % of a water-soluble solvent having 1 or 2 hydroxyl group(s) in single molecule;
(F) 0.1 to 0.5 mass % of a water-soluble polymer containing (meth)acrylic acid as a configuration unit and/or an acryloyl methyl taurate-vinylpyrrolidone copolymer;
(G) 0.01 to 1.0 mass % of a water-soluble inorganic salt and/or an organic salt having 1 to 8 carbon atoms; and
(H) water.

Alternatively, the skin cleansing agent composition of the present invention may be a skin cleansing agent composition having an isotropic liquid phase, which is a bicontinuous structure, and containing:
(A) 17 to 20 mass % of a nonionic surfactant having HLB of equal to or higher than 10 and equal to or lower than 17, containing a polyethylene glycol fatty acid ester, a polyoxyethylene glycerol fatty acid ester, a polyoxyethylene sorbitol fatty acid ester and an alkylpoly glucoside;
(B) 2.5 to 5 mass % of a nonionic surfactant having HLB of equal to or higher than 5 and equal to or lower than 8, and composed of diglyceryl isostearate and/or isostearyl glyceryl ether;
(C) 15 to 30 mass % of and oil agent, which is composed of (C1) hydrogenated polyisobutene and (C2) isopropyl myristate;
(D) 21 to 30 mass % of glycerol and/or sorbitol;
(E) 11 to 15 mass % of 1,3-butylene glycol and/or dipropylene glycol;
(F) 0.1 to 0.5 mass % of a water-soluble polymer containing (meth)acrylic acid as a configuration unit;
(G) 0.01 to 1.0 mass % of a water-soluble inorganic salt and/or an organic salt having 1 to 8 carbon atoms; and
(H) water,
in which the mass ratio of the aforementioned component (B) over the total mass of the aforementioned component (A) and the aforementioned component (B) being ((B)/((A)+(B))) is 0.1 to 0.2,
the mass ratio of the aforementioned component (F) over the total mass of the aforementioned component (A) and the aforementioned component (B) being ((F)/((A)+(B))) is 0.003 to 0.045,
the mass ratio of the aforementioned component (D) over the aforementioned component (E) being ((D)/(E)) is 0.1 to 2.5,
the mass ratio of the aforementioned component (G) over the aforementioned component (F) being ((F)/(G)) is 1 to 7 and preferably 2 to 7,
the mass ratio of the aforementioned component (C1) over the total mass of the aforementioned component (C2) and the aforementioned component (C3) being ((C1)/((C2)+(C3))) is 0.5 to 2, and
the mass ratio of the aforementioned component (C) over the mass of the component aforementioned (A) being ((C)/(A)) is 0.5 to 1.5.

The skin cleansing agent composition of the present invention may be produced by uniformly mixing all of the components that are solid at the ambient temperature after these are dissolved, regardless of the order for the mixing. For example, this can be produced by the following method. Specifically, the component (F) is dispersed in the component (H) water, and these are heated to a temperature of, preferably 70 degrees C. or higher to be equalized. On the other hand, concerning the raw materials that are solid at 20 degrees C. or concerning the raw materials for generating gel at an ambient temperature by being mixed with other component, these are heated to be melted, or these are dissolved in the other component that is not used for creating gel. Next, these are cooled to 25 degrees C., and then the other components are further mixed therein to be equalized to obtain the cleansing agent.

The skin cleansing agent composition of the present invention is preferably applied to, even more preferably a cleansing agent, a facial wash and the like. Alternatively, the skin cleansing agent composition of the present invention may also be impregnated into a base material such as a nonwoven fabric and the like to produce a sheet-shaped article, which can be employed for wiping makeup stains or sebum stains off.

The skin cleansing agent composition of the present invention contains the isotropic liquid phase that is in the bicontinuous structure. The isotropic liquid phase that is in the bicontinuous structure indicates an optically-isotropic transparent or translucent solution of low viscosity, in which both water and oil compose continuous phase. More specifically, this indicates a middle phase (or D phase) and a sponge phase (or L3 phase).

Further, the condition that the skin cleansing agent composition has the isotropic liquid phase that is bicontinuous structure in the present invention can be confirmed by: an observation of an appearance; an observation with an optical polarization microscope; a preparation of a phase diagram; a measurement of self-diffusion coefficient by nuclear magnetic resonance (NMR); a measurement of electric conductivity; a fluorescent probe method employing fluorochrome; and an electron microscope observation (transmission electron microscopy (TEM), scanning electron microscope (SEM)) by a freeze fracture replica method and the like. Simultaneous use of the observations of the appearance and via the light microscope, or simultaneous use of the observations of the appearance and via the polarizing plate is simple and easy and thus is preferable.

The cleansing agent having the bicontinuous structure has its appearance, which is transparent or translucent liquid, so that the isotropic liquid phase that is bicontinuous structure can be distinguished from other type of solutions. Here, the transparent or translucent employed in the present invention indicates the conditions, in which an optical transmittance measured at wavelength of 550 nm and cell length of 0.5 mm is equal to or higher than 20%. Also, the liquid state indicates the condition, in which viscosity at 30 degrees C. is equal to or lower than 10,000 mPa·s.

Also, when the polarization direction of two polarizing plates is adjusted to be mutually perpendicular, between which a sample in a transparent vessel is placed, it can confirm that it is isotropic by absence of transmission of light.

Further, the observation employing the optical polarization microscope is capable of achieving confirmation that it is isotropic by absence of transmission of light when the angle between the polarizing plates is 90 degrees.

When a quasi ternary phase equilibrium diagram composed of water phase (water and water-soluble solvent), oil phase (lipid component) and surfactant phase (hydrophilic nonionic surfactant and lipophilic nonionic surfactant) is employed, the confirmation on the isotropy can also be achieved by finding a feature on the phase diagram, in which it is the isotropic liquid condition and it is not a region continuing from an apex of the water phase or the oil phase. However, this sometimes cannot be applicable, depending on type of the substances to be employed, formulation of the water phase, and formulation of the surfactant phase.

The measurement of the self-diffusion coefficient via NMR is the method described in details by B. Lindman et al. in J. Colloid Interface Sci. 1981, 83, 569. The measurement of the electric conductivity, is the method described in details by M. Clausse et al. in "Microemulsion Systems" Marcel Dekker, New York, 1987, 387. The measurement via the fluorescent probe method employing the fluorochrome is the method described in details by B. K. Mishra et al. in Colloid Surface 1991, 56, 229.

The electron microscope observation via the freeze fracture replica method provides an image that a water phase and an oil phase form a continuous phase. More specifically, a structural body, in which a wholly rounded section and a moderately flat section are entangled to provide net-like feature and/or a layered structural body, in which a wholly rounded section and a moderately flat section are continued in disorder manner are observed. This observation can provide a confirmation that this is not a microemulsion, in which only water phase or only oil phase forms a continuous phase.

Also, a typical simplest method for confirming that the cleansing agent composition has the bicontinuous structure is a utilization of the condition, in which the water phase and the oil phase form a continuous phase, which includes: a liquid prepared by dissolving a water-soluble dye in water and a liquid prepared by dissolving an oil-soluble dye in oil are added to a test liquid in a static condition; and after leaving the test liquid for all night and all day, the confirmation can be achieved by the coloration condition presented by the test liquid. The color of the water-soluble dye is presented when the water phase forms the continuous phase. The color of the oil-soluble dye is presented when the oil phase forms the continuous phase. Both colors of the water-soluble dye and the oil-soluble dye are presented for the composition having the bicontinuous structure.

The viscosity of the skin cleansing agent composition of the present invention is preferably 100 to 2,000 mPa·s at 30 degrees C., and more preferably 300 to 1,500 mPa·s, and even more preferably 450 to 1,200 mPa·s. This allows improving the adhesiveness to the makeup to provide improved cleansing-ability, and avoiding drip of the liquid to provide enhanced usability. In addition to above, the viscosity of the skin cleansing agent composition of the present invention is measured with a Brookfield viscometer (rotor M-2, 12 rpm, 1 minute).

Also, the skin cleansing agent composition is required to have sufficient viscosity to be cohered to the makeup, in order to avoid the deterioration of the cleansing-ability in the case of being mixed with water. In order to achieve this, the viscosity of the diluted skin cleansing agent composition of the present invention diluted with an amount of water that is 1.25 times the mass of the skin cleansing agent composition is preferably equal to or higher than the non-diluted viscosity thereof, and more preferably equal to or larger than 1.05 times and equal to or lower than 1.5 times of the non-diluted viscosity thereof. This allows preventing a decrease of the viscosity in the case of handling with wet hand or wet skin, and therefore it is desirable that the adhesiveness to the makeup is not deteriorated and a concern of the drip of the liquid is avoided. More specifically, the viscosity at 30 degrees C. of the diluted skin cleansing agent composition of the present invention diluted with an amount of water that is 1.25 times the mass of the skin cleansing agent composition is preferably equal to or higher than 100 mPa·s.

Further, the skin cleansing agent composition of the present invention preferably also has the isotropic liquid phase that is the bicontinuous structure when this is diluted with water. This allows maintaining higher cleansing-ability in the case of handling with wet hand or wet skin. As described above, the isotropic liquid phase that is the bicontinuous structure can be distinguished from the other type of solution by the judgment of the appearance. More specifically, it is preferable that the skin cleansing agent composition of the present invention exhibits transparent or translucent appearance when it is diluted with an amount of water that is 1.25 times the mass of the skin cleansing agent composition. In addition to above, as described above, the transparent or the translucent employed in the present invention is indicated as exhibiting the optical transmittance measured at 550 nm of equal to or higher than 20%.

While the specific embodiments of the present invention have been described above, it is intended to present these embodiments for the purpose of illustrations of the present invention only, and various modifications other than that described above are also available. Concerning the embodiments described above, the present inventors will further disclose the following compositions or applications.

<1>

A typical composition is a skin cleansing agent composition having an isotropic liquid phase, which is a bicontinuous structure, and containing:

(A) 15 to 30 mass % of a nonionic surfactant having hydrophilic-lipophilic balance (HLB) of higher than 9 and equal to or lower than 20;

(B) 1 to 15 mass % of a nonionic surfactant having HLB of equal to or higher than 5 and equal to or lower than 9;

(C) 10 to 40 mass % of an oil agent, which is composed of (C1) a hydrocarbon oil, (C2) ester oil and/or (C3) an ether oil and exhibits a viscosity at 30 degrees C. of equal to or lower than 30 mPa·s;

(D) 10 to 40 mass % of a water-soluble solvent having 3 or more of hydroxyl groups in single molecule;

(E) 10 to 30 mass % of a water-soluble solvent having 1 or 2 hydroxyl group(s) in single molecule;

(F) 0.05 to 1.0 mass % of a water-soluble polymer containing (meth)acrylic acid as a configuration unit and/or an acryloyl methyl taurate-vinylpyrrolidone copolymer;

(G) 0.001 to 2.0 mass % of a water-soluble inorganic salt and/or an organic salt having 1 to 8 carbon atoms; and (H) water.

<2>

The typical composition may be the skin cleansing agent composition as described in the above <1>, in which the mass ratio of the component (B) over the total mass of the component (A) and the component (B) being ((B)/((A)+(B))) is equal to or higher than 0.05 and preferably equal to or higher than 0.1, and on the other hand is equal to or lower than 0.21 and preferably equal to or lower than 0.2.

<3>
The typical composition may be the skin cleansing agent composition as described in the above <1> or <2>, in which the mass ratio of the component (F) over the total mass of the component (A) and the component (B) being ((F)/((A)+(B))) is equal to or higher than 0.001 and preferably equal to or higher than 0.003, and on the other hand is equal to or lower than 0.06 and preferably equal to or lower than 0.045.

<4>
The typical composition may be the skin cleansing agent composition as described in any one of the above <1>, <2> and <3>, in which the mass ratio of the component (D) over the component (E) being ((D)/(E)) is equal to or higher than 0.1 and preferably equal to or higher than 1, and on the other hand is equal to or lower than 2.5.

<5>
The typical composition may be the skin cleansing agent composition as described in any one of the above <1> to <4>, in which the mass ratio of the aforementioned component (F) over the aforementioned component (G) being ((F)/(G)) is equal to or higher than 0.1, preferably equal to or higher than 1, and more preferably equal to or higher than 2, and on the other hand is equal to or lower than 10, and preferably equal to or lower than 7.

<6>
The typical composition may be the skin cleansing agent composition as described in any one of the above <1> to <5>, in which the mass ratio of the aforementioned component (C1) over the total mass of the aforementioned component (C2) and the aforementioned component (C3) being ((C1)/((C2)+(C3))) is equal to or higher than 0.3, and preferably equal to or higher than 0.5, and on the other hand is equal to or lower than 3, and preferably equal to or lower than 2.

<7>
The typical composition may be the skin cleansing agent composition as described in any one of the above <1> to <6>, in which the viscosity at 30 degrees C. of the skin cleansing agent composition is equal to or higher than 100 mPa·s, and preferably is equal to or higher than 300 mPa·s, and more preferably equal to or higher than 450 mPa·s, and on the other hand is equal to or lower than 2,000 mPa·s, preferably equal to or lower than 1,500 mPa·s, and more preferably equal to or lower than 1,200 mPa·s.

<8>
The typical composition may be the skin cleansing agent composition as described in any one of the above <1> to <7>, in which the viscosity at 30 degrees C. of the diluted skin cleansing agent composition of the present invention diluted with 1.25 times as much water is equal to or higher than 100 mPa·s, and exhibits transparent or translucent appearance.

<9>
The typical composition may be the skin cleansing agent composition as described in any one of the above <1> to <8>, in which the content of the ionic surfactant is equal to or lower than 0.05 mass %.

<10>
The typical composition may be the skin cleansing agent composition as described in any one of the above <1> to <9>, in which the content of water is preferably equal to or higher than 5 mass %, and more preferably equal to or higher than 10 mass %, and on the other hand is preferably equal to or lower than 50 mass %, more preferably equal to or lower than 40 mass % and further preferably equal to or lower than 30 mass %, and preferably 5 to 50 mass %, more preferably 10 to 40 mass %, and further preferably 10 to 30 mass %.

<11>
The typical composition may be the skin cleansing agent composition as described in any one of the above <1> to <10>, in which the content of the aforementioned component (A) is equal to or higher than 15 mass %, and preferably equal to or higher than 17 mass %, and on the other hand is equal to or lower than 30 mass %, and preferably equal to or lower than 20 mass %.

<12>
The typical composition may be the skin cleansing agent composition as described in any one of the above <1> to <11>, in which the content of the aforementioned component (B) is equal to or higher than 1 mass %, preferably equal to or higher than 2 mass %, and preferably equal to or higher than 2.5 mass %, and on the other hand is equal to or lower than 15 mass %, preferably equal to or lower than 10 mass %, and more preferably equal to or lower than 5 mass %.

<13>
The typical composition may be the skin cleansing agent composition as described in any one of the above <1> to <12>, in which the content of the aforementioned component (C) is equal to or higher than 10 mass %, and preferably equal to or higher than 15 mass %, and on the other hand is equal to or lower than 40 mass % and preferably equal to or lower than 30 mass %.

<14>
The typical composition may be the skin cleansing agent composition as described in any one of the above <1> to <13>, in which the content of the aforementioned component (D) is equal to or higher than 10 mass %, and preferably equal to or higher than 21 mass %, and on the other hand is equal to or lower than 40 mass %, and preferably equal to or lower than 30 mass %.

<15>
The typical composition may be the skin cleansing agent composition as described in any one of the above <1> to <14>, in which the content of the aforementioned component (E) is equal to or higher than 10 mass %, and preferably equal to or higher than 11 mass %, and on the other hand is equal to or lower than 30 mass %, preferably equal to or lower than 20 mass %, and more preferably equal to or lower than 15 mass %.

<16>
The typical composition may be the skin cleansing agent composition as described in any one of the above <1> to <15>, in which the content of the aforementioned component (F) is equal to or higher than 0.05 mass %, and preferably equal to or higher than 0.1 mass %, and on the other hand is equal to or lower than 1.0 mass %, preferably equal to or lower than 0.8 mass %, and more preferably equal to or lower than 0.5 mass %.

<17>
The typical composition may be the skin cleansing agent composition as described in any one of the above <1> to <16>, in which the content of the aforementioned component (G) is equal to or higher than 0.001 mass %, preferably equal to or higher than 0.005 mass %, and more preferably equal to or higher than 0.01 mass %, and on the other hand is equal to or lower than 2.0 mass %, and preferably equal to or lower than 1.0 mass %.

<18>
The typical composition may be the skin cleansing agent composition as described in any one of the above <1> to <17>, in which, in the aforementioned component (A), HLB is larger than 9, and preferably equal to or higher than 10, and on the other hand is equal to or lower than 20, and preferably equal to or lower than 17.

<19>

The typical composition may be the skin cleansing agent composition as described in any one of the above <1> to <18>, in which the aforementioned component (A) is one, or two to five selected from the group consisting of: fatty acid polyglycerides; polyethylene glycol fatty acid esters; polyoxyethylene glycerol fatty acid esters; propylene glycol fatty acid esters; polyoxyethylene polyoxypropylene glycol esters; sorbitan fatty acid esters; polyoxyethylene sorbitan fatty acid esters; polyoxyethylene sorbitol fatty acid esters; polyoxyethylene castor oil; polyoxyethylene hydrogenated castor oil; polyoxyethylene hydrogenated castor oil fatty acid esters; polyalkyl glyceryl ethers; polyoxyethylene alkyl ethers; polyoxyethylene alkyl ether fatty acid esters; saccharose fatty acid esters; alkyl polyglucosides; alkyl glyceryl ethers and the like.

<20>

The typical composition may be the skin cleansing agent composition as described in any one of the above <1> to <19>, in which the aforementioned component (A) is one, or two to five preferably selected from the group consisting of: fatty acid polyglycerides; polyethylene glycol fatty acid esters; polyoxyethylene glycerol fatty acid esters; polyoxyethylene sorbitol fatty acid esters; alkyl glyceryl ethers; polyoxyethylene alkyl ethers; saccharose fatty acid esters and alkylpoly glucosides are advantageous, and more preferably selected from the group consisting of: polyethylene glycol fatty acid ester, polyoxyethylene glycerol fatty acid ester, polyoxyethylene sorbitol fatty acid ester and alkylpoly glucoside.

<21>

The typical composition may be the skin cleansing agent composition as described in any one of the above <1> to <20>, in which the aforementioned component (A) is one or more selected from the group consisting of: a polyethylene glycol fatty acid ester, a polyoxyethylene glycerol fatty acid ester, a polyoxyethylene sorbitol fatty acid ester and an alkylpoly glucoside, and preferably contains at least a polyoxyethylene glycerol fatty acid ester and a polyethylene glycol fatty acid ester, and more preferably contains all of: a polyethylene glycol fatty acid ester, a polyoxyethylene glycerol fatty acid ester, a polyoxyethylene sorbitol fatty acid ester and an alkylpoly glucoside.

<22>

The typical composition may be the skin cleansing agent composition as described in any one of the above <1> to <21>, in which the content of a silicone based surfactant is preferably equal to or lower than 1 mass %, and more preferably equal to or lower than 0.1 mass %, and it even more preferably contains no silicone based surfactant.

<23>

The typical composition may be the skin cleansing agent composition as described in any one of the above <1> to <22>, in which the aforementioned component (B) has HLB of equal to or higher than 5 and equal to or lower than 9, and preferably equal to or lower than 8.

<24>

The typical composition may be the skin cleansing agent composition as described in any one of the above <1> to <23>, in which the aforementioned component (B) is one or more selected from fatty acid polyglyceride, polyglycerol alkylethers, and polyethylene glycol fatty acid ester, and preferably selected from diglyceryl oleate, diglyceryl isostearate, diglycerol 2-ethylhexyl ether, isostearyl glyceryl ether and polyethylene glycol (5) monostearic acid ester.

<25>

The typical composition may be the skin cleansing agent composition as described in any one of the above <1> to <24>, in which the aforementioned component (C) is configured of an oil agent composed of being (C1) hydrocarbon oils and (C2) ester oils and/or (C3) ether oils

<26>

The typical composition may be the skin cleansing agent composition as described in any one of the above <1> to <25>, in which the aforementioned component (C1) is one or more selected from liquid paraffin, liquid isoparaffin, light liquid isoparaffin and scualane, and is preferably liquid isoparaffin, and is more preferably hydrogenated poly isobutene, and is further preferably hydrogenated poly isobutene having the polymerization degree of isobutene of 3 to 6.

<27>

The typical composition may be the skin cleansing agent composition as described in any one of the above <1> to <26>, in which the aforementioned component (C2) selected from cholesteryl isostearate, isopropyl palmitate, isopropyl myristate, isopropyl isostearate, octadecyl myristate, cetyl 2-ethylhexanoate, isononyl isononanoate, isotridecyl isononanoate, neopentylglycol dicaprate, tri(2-ethylhexanoate) glycerol, and tri(caprylate/caprate) glycerol.

<28>

The typical composition may be the skin cleansing agent composition as described in any one of the above <1> to <27>, in which the aforementioned component (C3) is selected from alkyl-1,3-dimethylbutyl ether, dioctyl ether and nonylphenyl ether.

<29>

The typical composition may be the skin cleansing agent composition as described in any one of the above <1> to <28>, in which the aforementioned component (C) contains a combination of component (C1): isoparaffin selected from liquid isoparaffin, light liquid isoparaffin and hydrogenated polyisobutene, and component (C2) one or more selected from isopropyl myristate, isopropyl palmitate and isononyl isononanoate, and preferably contains a combination of isoparaffin, especially liquid isoparaffin, and isopropyl myristate, and further preferably contains a combination of (C1) liquid isoparaffin and (C2) isopropyl myristate.

<30>

The typical composition may be the skin cleansing agent composition as described in any one of the above <1> to <29>, in which the aforementioned component (D) is preferably one or more selected from glycerol, diglycerol, sorbitol, maltitol, maltose, fructose, xylitol, maltotriose, threitol, erythritol, glucose, methylglucoside and ethyl glucoside, and more preferably one or more selected from glycerol, sorbitol and maltitol, and is further preferably one or more selected from glycerol and sorbitol.

<31>

The typical composition may be the skin cleansing agent composition as described in any one of the above <1> to <30>, in which the aforementioned component (E) is one or more selected from ethanol, propanol, isopropanol, butanol, isobutanol, ethylene glycol, propylene glycol, diethylene glycol, dipropylene glycol, 1,3-butylene glycol, 1,4-butylene glycol, hexylene glycol and isoprene glycol, and is more preferably one or more selected from 1,3-butylene glycol, isoprene glycol, propylene glycol and dipropylene glycol.

<32>

The typical composition may be the skin cleansing agent composition as described in any one of the above <1> to <31>, in which the water-soluble polymer containing (meth) acrylic acid of the aforementioned component (F) as the structural unit is preferably employed by neutralizing all of or a portion of the unit of (meth)acrylic acid with an alkali agent.

The typical composition may be the skin cleansing agent composition as described in any one of the above <1> to <32>, in which the alkali agent for neutralizing the water-soluble polymer containing (meth)acrylic acid of the aforementioned component (F) as the structural unit is one, two or more of potassium hydroxide and sodium hydroxide, and the content of the alkali agent is equal to or larger than 0.01 mass % and equal to or lower than 1.0 mass %.

<34>

The typical composition may be the skin cleansing agent composition as described in any one of the above <1> to <33>, in which pH is 5.5 to 9, and preferably 6 to 8.

<35>

The typical composition may be the skin cleansing agent composition as described in any one of the above <1> to <34>, in which the aforementioned component (G) is one, two or more selected from water-soluble inorganic salts and/or organic salts having 1 to 8 carbon atoms.

<36>

The typical composition may be the skin cleansing agent composition as described in any one of the above <1> to <35>, in which the water-soluble inorganic salt of the aforementioned component (G) is one or more selected from sodium chloride, potassium chloride, magnesium chloride, sodium sulfate, potassium sulfate, magnesium sulfate, aluminum sulfate, sodium carbonate and sodium hydrogen carbonate.

<37>

The typical composition may be the skin cleansing agent composition as described in any one of the above <1> to <36>, in which the water-soluble organic salt of the aforementioned component (G) is one or more selected from: alkali metal salts of acid selected from lactic acid, succinic acid, citric acid, tartaric acid, malic acid, maleic acid and fumaric acid; and ammonium salt of the aforementioned acids, and preferably one or more selected from monosodium citrate, disodium citrate, trisodium citrate, potassium lactate, ammonium succinate, potassium malate and sodium malate, and more preferably one or two or more selected from monosodium citrate, disodium citrate, trisodium citrate and sodium malate.

<38>

The typical composition may be the skin cleansing agent composition as described in any one of the above <1> to <37>, in which the aforementioned component (G) contains none of an amino acid or a compound constituting inner salt.

<39>

The typical composition may be the skin cleansing agent composition as described in any one of the above <1> to <38>, in which the aforementioned component (G) is preferably an inorganic salt, and is more preferably one or more selected from sodium chloride and potassium chloride, and is further preferably potassium chloride.

<40>

A use of the skin cleansing agent composition as described in any one of the above <1> to <39>, by applying it over makeup skin to remove a makeup cosmetic composition.

<41>

A use of the skin cleansing agent composition as described in any of the above <1> to <39>, for producing makeup cosmetic composition-cleansing agent, which is applied over a makeup skin to remove the makeup cosmetic composition.

<42>

A use of the skin cleansing agent composition as described in any of the above <1> to <39>, by applying it over hand and/or skin wet with water to remove a makeup cosmetic composition.

<43>

A use of the skin cleansing agent composition as described in any of the above <1> to <39>, for producing a makeup cosmetic composition-cleansing agent, which is applied over hand and/or skin wet with water to remove the makeup cosmetic composition.

EXAMPLES

Next, the present invention will be further described in reference to Examples, though it is not intended to limit the scope of the present invention.

Examples 1 to 21, Comparative Examples 1 to 6

Skin cleansing agent compositions having formulations shown in Tables 1 to 4 were produced along the following production method, and were evaluated. Here, units for the content of the respective components in the Tables are represented by mass % over the whole skin cleansing agent composition.

(Production Method)

The component F was dispersed in the component C, and the obtained mixture was added to the component H that was heated to 80 degrees C. and was stirred. Subsequently, potassium hydroxide was added therein to provide pH of about 7. The component H, the component C and the component F were uniformly mixed, and then the mixture was cooled to 25 degrees C., and consecutively, the component A, the component B, the component D, the component E and the component G were uniformly added to produce a skin cleansing agent composition.

(Evaluations)

1. Condition with Room Temperature (25 Degrees)

The presence of the bicontinuous structure in the skin cleansing agent compositions in respective Examples and Comparative Examples were detected according to the method, in which one drop of each of "Blue No. 1" (Brilliant Blue FCF) which is water-soluble pigment (0.1% aqueous solution) and "Red No. 103" (eosine) which is oil-soluble pigment (red) (0.1% liquid paraffin solution) was added in products of Example and Comparative Example in a standing-still condition, and after leaving for one night and day, coloration condition thereof was confirmed. When blue color was observed, it was confirmed that the continuous phase was an aqueous solvent. On the other hand, when red color was observed, it was confirmed that the continuous phase was a lipid solvent. On the contrary, when purple color (color mixture of red and blue) was observed, it was confirmed that the continuous phase contained an aqueous solvent and a lipid solvent, and therefore confirmed that the phase is configured of a bicontinuous structure. In the skin cleansing agent compositions of Examples 1 to 21, when the oil-soluble pigment was added, red color was observed, when the water-soluble pigment was added, blue color was observed, and when both of the oil-soluble pigment and the water-soluble pigment were added, purple color was observed. Consequently, it was confirmed that the skin cleansing agent compositions of Examples 1 to 21 had the bicontinuous structure.

2. Viscosity (1)

Here, the viscosity of each of the oil agents in the components (C1), (C2) and (C3) was measured by employing BM type viscometer (commercially available from TOKIMEC Co., Ltd., measurement conditions: rotor No. 1, 60 rpm, for one minute).

(2)

The viscosity of each of the skin cleansing agent compositions of respective Examples and Comparative Examples was measured by employing a measuring device: TVB-10M commercially available from TOKI SANGYO CO., LTD), with rotor No. M-2, at 12 rpm and for one minute to measure respective viscosities at 30 degrees C. The results are shown in Tables 1 to 4.

3. Appearance when Diluted with 1.25 Times as Much Water

A measuring device: UV-1800 (commercially available from Shimadzu Co., Ltd.) was employed, and each of the skin cleansing agent compositions of respective Examples and Comparative Examples was added in a cell having a light path length of 0.5 mm to measure transmissivity in wavelength 550 nm. The result of higher than 80% was defined as being transparent, the result within a range of 20 to 80% was defined as being translucent, and the result of lower than 20% was defined as being opaque. The results are shown in Tables 1 to 4.

4. Cleansing-Ability 10 mg of Waterproof type mascara (Commercially available from Maybelline Inc., "Volume Express Hyper Curl Waterproof") was applied over the arm of a specialty panelist, and after one hour, 100 mg of each of the skin cleansing agent compositions of respective Examples and Comparative Examples was taken, and 10 times of massages at constant force and speed were conducted and after the rinsing was conducted with water. After having been rinsed with a water of 30 degrees, the evaluation was carried out by the following references. The results are shown in Tables 1 to 4.

A: very much removed;
B: much removed;
C: moderately removed; and
D: hardly removed.

5. Difficulty in Dripping of Rinsing Solution 0.7 g of the liquid was uniformly applied over 84 cm² of an acrylic flat plate, and then the plate was turned to the vertical position. After 30 seconds was passed, the portion of the liquid adhered on the upper quarter section of the plate was wiped off to be collected. Evaluations were carried out with the following references on the basis of ratio of the amount of the collected liquid per area over the amount of the uniformly coated solution per area (8.3 mg/cm²). The results are shown in Tables 1 to 4.

A: equal to or higher than 80%;
B: 79% to 70%;
C: 69 to 50%; and
D: equal to or lower than 50%.

6. Spreading-Ability 1 g of the skin cleansing agent compositions of respective Example and Comparative Examples was taken, and was applied on a forearm of a specialty panelist and massage was conducted at constant force and speed, and the results were evaluated with the following references. The results are shown in Tables 1 to 4.

A: very much spread;
B: much spread;
C: moderately spread; and
D: poorly spread.

7. Rinsing-Ability

About 2 g of each of the skin cleansing agent compositions in respective Examples and Comparative Examples was applied on a forearm of a specialty panelist, and the rinsing-ability when rinsed with water of 30 degrees C. was evaluated with the following references. The results are shown in Tables 1 to 4.

A: sliminess feel disappeared very quickly, and thus was very easy to be rinsed off;
B: sliminess feel disappeared quickly, and thus was easy to be rinsed off;
C: sliminess feel disappeared less quickly, and thus was difficult to be rinsed off; and
D: sliminess feel remained, and thus was not able to be rinsed off.

8. Stability

Each of the skin cleansing agent compositions of respective Examples and Comparative Examples was supplied in a covered glass vessel, and then was stored at respective temperatures for one day, and the evaluation was carried out with the following references. The results are shown in Tables 1 to 4.

○ (circle); no change; and
x (cross); separated.

TABLE 1

| RAW MATERIALS | COMPONENTS | EXAMPLES |  |  |  |  |  |  |  |
|---|---|---|---|---|---|---|---|---|---|
| | | 1 | 2 | 3 | 4 | 5 | 6 | 7 | 8 |
| COMPONENT (A) AG-10LK (HLB = 17) (40%) (KAO) | ALKYL (8 TO 16 CARBON ATOMS) POLYGLUCOSIDE | 7.50 | 7.50 | 7.50 | 7.50 | 7.50 | 7.50 | 7.50 | 7.50 |
| LEVENOL C-301 (HLB = 13) (KAO) | POLYOXYETHYLENE GLYCEROL COCOATE | 13.50 | 7.00 | 7.00 | 7.00 | 7.00 | 7.00 | 6.75 | 7.50 |
| EMANON 1112 (HLB = 14) (KAO) | POLYETHYLENGYCOL MONOLAURATE | | 6.50 | 6.50 | 6.50 | 6.50 | 6.50 | 4.75 | 6.50 |
| RHEODOL 430V (HLB = 10.5) (KAO) | POLYOXYETHYLENE SORBITOL TETRAOLEATE | 3.00 | 3.00 | 3.00 | 3.00 | 3.00 | 3.00 | 3.00 | 3.00 |
| COMPONENT (B) COSMOL 41V (HLB = 8) NISSIN OILIO) | POLYGLYCERYL MONOISOSTEARATE | 2.50 | 2.50 | 2.50 | 2.50 | 2.50 | 2.50 | 4.50 | 2.00 |
| COMPONENT (C1) PARLEAM EX (17 mPa · s) (NOF CORP.) | LIQUID ISOPARAFFIN | 10.00 | 10.00 | 10.00 | 10.00 | 10.00 | 10.00 | 4.80 | 10.00 |
| PARLEAM 4 (3 mPa · s) (NOF CORP.) | LIGHT LIQUID ISOPARAFFIN | | | | | | | 5.20 | |
| COMPONENT (C2) EXCEPARL IPM (10 mPa · s) (KAO) | ISOPROPYL MYRISTATE | 10.00 | 10.00 | 10.00 | 5.00 | 5.00 | 10.00 | 15.00 | 10.00 |
| EXCEPARL IPP (10 mPa · s) (KAO) | ISOPROPYL PALMITATE | | | | 5.00 | | | | |
| COMPONENT (C3) ASE-166K (8 mPa · s) (KAO) | ALKYL-1,3-DIMETHYLBUTYL ETHER | | | | | 5.00 | | | |
| COMPONENT (D) CETIOL OE (5 mPa · s) (COGNIS) | DIOCTYL ETHER | 17.00 | 17.00 | 17.00 | 17.00 | 17.00 | 17.00 | 17.00 | 17.00 |
| GLYCERIN (COSMETIC GRADE) (100%) (KAO) | GLYCERIN | 8.85 | 8.85 | 8.85 | 4.95 | 4.95 | 8.85 | 4.95 | 8.85 |
| SORBITOL #650 (70%) (KAO) | SORBIT SOLUTION | 13.85 | 13.85 | 13.85 | 14.50 | 14.50 | | 14.50 | 13.85 |
| 1,3-BUTYLENE GLYCOL-P | 1,3-BUTYLENE GLYCOL | | | | | | | | |
| DIPROPYLENE GLYCOL DPG-FC (ASAHI GLASS CO.) | DIPROPYLENE GLYCOL | | | | | | 11.00 | | |
| COMPONENT (E) PEMULEN TR-2 (LUBRIZOL) | ACRYLIC ACID-ALKYL METHACRYLATE COPOLYMER | 0.20 | 0.20 | 0.20 | 0.20 | 0.20 | 0.20 | 0.20 | 0.20 |
| COMPONENT (F) POTASSIUM CHLORIDE | POTASSIUM CHLORIDE | 0.05 | 0.05 | 0.05 | 0.05 | 0.05 | 0.05 | 0.05 | 0.05 |
| COMPONENT (H) PURIFIED WATER | PURIFIED WATER | BALANCE | BALANCE | BALANCE | BALANCE | BALANCE | BALANCE | BALANCE | BALANCE |
| POTASSIUM HYDROXIDE SOLUTION (48%) | POTASSIUM HYDROXIDE SOLUTION | 0.12 | 0.12 | 0.12 | 0.12 | 0.12 | 0.12 | 0.12 | 0.12 |
| FRAGRANCE | | 0.30 | 0.30 | 0.30 | 0.30 | 0.30 | 0.30 | 0.30 | 0.30 |
| B/(A + B) | | 100.00 | 100.00 | 100.00 | 100.00 | 100.00 | 100.00 | 100.00 | 100.00 |
| F/(A + B) | | 0.11 | 0.11 | 0.11 | 0.11 | 0.11 | 0.11 | 0.20 | 0.09 |
| D/E | | 0.009 | 0.009 | 0.009 | 0.009 | 0.009 | 0.009 | 0.009 | 0.009 |
| F/G | | 1.67 | 1.67 | 1.67 | 1.41 | 1.41 | 2.11 | 1.41 | 1.67 |
| C1/(C2 + C3) | | 4.00 | 4.00 | 4.00 | 4.00 | 4.00 | 4.00 | 4.00 | 4.00 |
| VISCOSITY (mPa · s) | | 1.00 | 1.00 | 1.00 | 1.00 | 1.00 | 1.00 | 0.67 | 1.00 |
| | | 501 | 684 | 699 | 584 | 604 | 690 | 630 | 655 |
| VISCOSITY WHEN DILUTED WITH 1.25 TIMES AS MUCH WATER (mPa · s) | | 558 | 745 | 780 | 650 | 650 | 766 | 705 | 735 |
| APPEARANCE WHEN DILUTED WITH 1.25 TIMES AS MUCH WATER | | TRANSLUCENT | TRANSLUCENT | TRANSLUCENT | TRANSLUCENT | TRANSLUCENT | TRANSLUCENT | TRANSLUCENT | TRANSLUCENT |

TABLE 1-continued

| RAW MATERIALS | COMPONENTS | 1 | 2 | 3 | 4 | 5 | 6 | 7 | 8 |
|---|---|---|---|---|---|---|---|---|---|
| CLEANSING-ABILITY (WP MASCARA) | | B | B | B | A | A | B | A | B |
| APPLICATION-ABILITY | | A | A | A | A | A | A | A | A |
| SPREADING-ABILITY | | A | A | A | A | A | A | A | A |
| RINSING-ABILITY | | A | A | A | A | A | A | A | A |
| CONDITION AT ROOM TEMPERATURE | | SINGLE LIQUID PHASE | SINGLE LIQUID PHASE | SINGLE LIQUID PHASE | SINGLE LIQUID PHASE | SINGLE LIQUID PHASE | SINGLE LIQUID PHASE | SINGLE LIQUID PHASE | SINGLE LIQUID PHASE |
| STABILITY (50° C.) | | ○ | ○ | ○ | ○ | ○ | ○ | ○ | X |
| STABILITY (40° C.) | | ○ | ○ | ○ | ○ | ○ | ○ | ○ | ○ |
| STABILITY (25° C.) | | ○ | ○ | ○ | ○ | ○ | ○ | ○ | ○ |
| STABILITY (5° C.) | | ○ | ○ | ○ | ○ | ○ | ○ | ○ | ○ |
| STABILITY (−5° C.) | | X SEPERATED | | | | | | | ○ |

TABLE 2

| | RAW MATERIALS | COMPONENTS | EXAMPLES | | | | | | | |
|---|---|---|---|---|---|---|---|---|---|---|
| | | | 9 | 10 | 11 | 12 | 13 | 14 | 15 | 16 |
| COMPONENT (A) | AG-10LK (HLB = 17) (40%) (KAO) | ALKYL (8 TO 16 CARBON ATOMS) POLYGLUCOSIDE | 7.50 | 7.50 | 7.50 | 7.50 | 7.50 | 7.50 | 7.50 | 7.50 |
| | LEVENOL C-301 (HLB = 13) (KAO) | POLYOXYETHYLENE GLYCERYL COCOATE | 7.00 | 6.00 | 7.00 | 7.00 | 7.00 | 7.00 | 7.00 | 7.00 |
| | EMANON 1112 (HLB = 14) (KAO) | POLYETHYLENGLYCOL MONOLAURATE | 6.50 | 6.00 | 6.50 | 6.50 | 6.50 | 6.50 | 6.50 | 6.50 |
| | RHEODOL 430V (HLB = 10.5) (KAO) | POLYOXYETHYLENE SORBITOL TETRAOLEATE | 3.00 | 3.00 | 3.00 | 3.00 | 3.00 | 3.00 | 3.00 | 3.00 |
| COMPONENT (B) | COSMOL 41V (HLB = 8) (NISSIN OILIO) | POLYGLYCERYL MONOISOSTEARATE | 2.50 | 4.00 | 2.50 | 2.50 | 2.50 | 2.50 | 2.50 | |
| | PENETOL GE-IS (HLB = 5) (KAO) | ISOSTEARYL GLYCERYL ETHER | | | | | | | | 2.20 |
| COMPONENT (C1) | PARLEAM EX (17 mPa · s) (NOF CORP.) | LIQUID ISOPARAFFIN | 10.00 | 12.50 | 10.00 | 10.00 | 10.00 | 10.00 | 10.00 | 10.00 |
| COMPONENT (C2) | EXCEPARL IPM (10 mPa · s) (KAO) | ISOPROPYL MYRISTATE | 10.00 | 12.50 | 10.00 | 10.00 | 10.00 | 10.00 | 10.00 | 10.00 |
| COMPONENT (D) | GLYCERIN (COSMETIC GRADE) (100%) (KAO) | GLYCERIN | 17.00 | 19.20 | 17.00 | 17.00 | 19.20 | 17.00 | 17.00 | 17.00 |
| | SORBITOL #650 (7%) (KAO) | SORBIT SOLUTION | 8.85 | 6.25 | 8.85 | 8.85 | 6.25 | 8.85 | 8.85 | 8.85 |
| | 1,3-BUTYLENE GLYCOL-P | 1,3-BUTYLENE GLYCOL | 13.85 | 11.00 | 13.85 | 13.85 | 11.00 | 13.85 | 13.85 | 13.85 |
| COMPONENT (E) | PEMULEN TR-2 (LUBRIZOL) | ACRYLIC ACID-ALKYL METHACRYLATE COPOLYMER | 1.00 | 0.20 | 0.30 | 0.10 | 0.10 | 0.10 | 0.13 | 0.20 |
| | PEMULEN TR-1 (LUBRIZOL) | ACRYLIC ACID-ALKYL METHACRYLATE COPOLYMER | | | | | 0.10 | | | |
| COMPONENT (F) | ARISTOFLEX AVC (CLARIANT) | (ACRYLOYL DIMETHYL AMMONIUM/VP) COPOLYMER | | | | | | 0.10 | | |
| COMPONENT (G) | POTASSIUM CHLORIDE | POTASSIUM CHLORIDE | 0.20 | 0.03 | 0.03 | | 0.03 | 0.05 | | 0.05 |
| | SODIUM CHLORIDE | SODIUM CHLORIDE | | | | | | | 0.08 | |
| | DIPOTASSIUM CITRATE | DIPOTASSIUM CITRATE | | | | 0.56 | | | | |
| COMPONENT (H) | PURIFIED WATER | PURIFIED WATER | BALANCE | BALANCE | BALANCE | BALANCE | BALANCE | BALANCE | BALANCE | BALANCE |
| | POTASSIUM HYDROXIDE SOLUTION (48%) | POTASSIUM HYDROXIDE SOLUTION | 0.12 | 0.12 | 0.18 | 0.06 | 0.12 | 0.06 | 0.08 | 0.12 |
| | FRAGRANCE | | 0.30 | 0.30 | 0.30 | 0.30 | 0.30 | 0.30 | 0.30 | 0.30 |

TABLE 2-continued

| RAW MATERIALS COMPONENTS | EXAMPLES | | | | | | | |
|---|---|---|---|---|---|---|---|---|
| | 9 | 10 | 11 | 12 | 13 | 14 | 15 | 16 |
| | 100.00 | 100.00 | 100.00 | 100.00 | 100.00 | 100.00 | 100.00 | 100.00 |
| B/(A + B) | 0.11 | 0.18 | 0.11 | 0.11 | 0.11 | 0.11 | 0.11 | 0.10 |
| F/(A + B) | 0.045 | 0.009 | 0.014 | 0.005 | 0.009 | 0.009 | 0.006 | 0.010 |
| D/E | 1.67 | 2.14 | 1.67 | 1.67 | 2.14 | 1.67 | 1.67 | 1.67 |
| F/G | 5.00 | 6.67 | 10.00 | 0.18 | 6.67 | 4.00 | 1.73 | 4.00 |
| C1/(C2 + C3) | 1.00 | 1.00 | 1.00 | 1.00 | 1.00 | 1.00 | 1.00 | 1.00 |
| VISCOSITY (mPa · s) | 1602 | 568 | 1455 | 170 | 474 | 725 | 206 | 689 |
| VISCOSITY WHEN DILUTED WITH 1.25 TIMES AS MUCH WATER (mPa · s) | 2320 | 645 | 1905 | 152 | 542 | 850 | 228 | 720 |
| APPEARANCE WHEN DILUTED WITH 1.25 TIMES AS MUCH WATER | TRANS LUCENT | TRANS LUCENT | TRANS LUCENT | TRANS LUCENT | TRANS LUCENT | TRANS LUCENT | TRANS LUCENT | TRANS LUCENT |
| CLEANSING-ABILITY (WP MASCARA) | B | A | B | B | B | B | B | B |
| APPLICATION-ABILITY | A | A | A | A | A | A | A | A |
| SPREADING-ABILITY | B | A | B | A | A | A | A | A |
| RINSING-ABILITY | B | A | A | A | A | A | A | A |
| CONDITION AT ROOM TEMPERATURE | SINGLE LIQUID PHASE | SINGLE LIQUID PHASE | SINGLE LIQUID PEASE | SINGLE LIQUID PHASE | SINGLE LIQUID PHASE | SINGLE LIQUID PHASE | SINGLE LIQUID PHASE | SINGLE LIQUID PAASE |
| STABILITY (50° C.) | ○ | ○ | ○ | ○ | ○ | ○ | ○ | ○ |
| STABILITY (40° C.) | ○ | ○ | ○ | ○ | ○ | ○ | ○ | ○ |
| STABILITY (25° C.) | ○ | ○ | ○ | ○ | ○ | ○ | ○ | ○ |
| STABILITY (5° C.) | ○ | ○ | ○ | ○ | ○ | ○ | ○ | ○ |
| STABILITY (−5° C.) | ○ | ○ | ○ | ○ | ○ | ○ | ○ | ○ |

TABLE 3

| COMPONENT | RAW MATERIALS | COMPONENTS | COMPARATIVE EXAMPLES 1 | 2 | 3 | 4 | 5 | 6 |
|---|---|---|---|---|---|---|---|---|
| COMPONENT (A) | AG-10LK (HLB = 17) (40%) (KAO) | ALKYL (8 TO 16 CARBON ATOMS) POLYGLUCOSIDE | 7.50 | 7.50 | 7.50 | 7.50 | 7.50 | 10.00 |
| | LEVENOL C-301 (HLB = 13) (KAO) | POLYOXYETHYLENE GLYCERYL COCOATE | 13.50 | 13.50 | 13.50 | 13.50 | 13.50 | |
| | EMANON 1112 (HLB = 14) (KAO) | POLYETHYLENGLYCOL MONOLAURATE | | | | | | 14.00 |
| | RHEODOL 430V (HLB = 10.5) (KAO) | POLYOXYETHYLENE SORBITOL TETRAOLEATE | 3.00 | 3.00 | 3.00 | 3.00 | 3.00 | |
| COMPONENT (B) | COSMOL 41V (HLB = 8) (NISSIN OILIO) | POLYGLYCERYL MONOISOSTEARATE | 2.50 | 2.50 | 2.50 | 2.50 | 2.50 | 7.00 |
| COMPONENT (C1) | PARLEAM EX (17 mPa·s) (NOF CORP.) | LIQUID ISOPARAFFIN | 10.00 | 10.00 | 10.00 | | | |
| | PARLEAM 4 (3 mPa·s) (NOF CORP.) | LIGHT LIQUID ISOPARAFFIN | 10.00 | 10.00 | 10.00 | 20.00 | 20.00 | 15.00 |
| COMPONENT (C2) | EXCEPARL IPM (10 mPa·s) (KAO) | ISOPROPYL MYRISTATE | | | | | | |
| COMPONENT (D) | GLYCERIN (COSMETIC GRADE) (100%) (KAO) | GLYCERIN | 17.00 | 17.00 | 17.00 | 17.00 | 17.00 | |
| COMPONENT (E) | SORBITOL #650 (70%) (KAO) | SORBIT SOLUTION | 8.85 | 8.85 | 8.85 | 8.85 | 8.85 | 15.00 |
| | 1,3-BUTYLENE GLYCOL-P | 1,3-BUTYLENE GLYCOL | 13.85 | 13.85 | 13.85 | 13.85 | 13.85 | 15.00 |
| COMPONENT (F) | PEMULEN TR-2 (LUBRIZOL) | ACRYLIC ACID-ALKYL METHACRYLATE COPOLYMER | | 0.20 | | 0.20 | 0.20 | |
| COMPONENT (G) | POTASSIUM CHLORIDE | POTASSIUM CHLORIDE | | | 0.05 | 0.05 | 0.05 | |
| COMPONENT (H) | PURIFIED WATER | PURIFIED WATER | BALANCE | BALANCE | BALANCE | BALANCE | BALANCE | BALANCE |
| | POTASSIUM HYDROXIDE SOLUTION (48%) | POTASSIUM HYDROXIDE SOLUTION | | 0.12 | 0.12 | 0.12 | 0.12 | |
| | FRAGRANCE | | 0.30 | 0.30 | 0.30 | 0.30 | 0.30 | 0.30 |
| B/(A + B) | | | 100.00 | 100.00 | 100.00 | 100.00 | 100.00 | 100.00 |
| F/(A + B) | | | 0.11 | 0.11 | 0.11 | 0.11 | 0.11 | 0.28 |
| D/E | | | 0.00 | 0.01 | 0.00 | 0.01 | 0.01 | 0.00 |
| F/G | | | 1.67 | 1.67 | 1.67 | 1.67 | 1.67 | 0.70 |
| C1/(C2 + C3) | | | — | — | — | — | — | — |
| VISCOSITY (mPa·s) | | | 1.00 | 1.00 | 1.00 | 4.00 | 4.00 | 55 |
| VISCOSITY WHEN DILUTED WITH 1.25 TIMES AS MUCH WATER (mPa·s) | | | — | — | — | — | — | 38 |
| APPEARANCE WHEN DILUTED WITH 1.25 TIMES AS MUCH WATER | | | — | — | — | — | — | TRANSLUCENT |
| CLEANSING-ABILITY (WP MASCARA) | | | — | — | — | — | — | A |
| APPLICATION-ABILITY | | | — | — | — | — | — | D |
| SPREADING-ABILITY | | | — | — | — | — | — | D |
| RINSING-ABILITY | | | — | — | — | — | — | A |
| CONDITION AT ROOM TEMPERATURE | | | SEPARATED (D + O) | SEPARATED (D + O) | SEPARATED (D + O) | SEPARATED (D + O) | SEPARATED (D + O) | SINGLE LIQUID PHASE |
| STABILITY (50° C.) | | | — | — | — | — | — | ○ |
| STABILITY (40° C.) | | | — | — | — | — | — | ○ |
| STABILITY (25° C.) | | | — | — | — | — | — | ○ |
| STABILITY (5° C.) | | | — | — | — | — | — | ○ |
| STABILITY (−5° C.) | | | — | — | — | — | — | ○ |

TABLE 4

| | RAW MATERIALS | COMPONENTS | EXAMPLES | | | | |
|---|---|---|---|---|---|---|---|
| | | | 17 | 18 | 19 | 20 | 21 |
| COMPONENT (A) | AG-10LK (HLB = 17) (40%) (KAO) | ALKYL (8 TO 16 CARBON ATOMS POLYGLUCOSIDE | 7.50 | 7.50 | 7.50 | 7.50 | 7.50 |
| | LEVENOL C-301 (HLB = 13) (KAO) | POLYOXYETHYLENE GLYCERYL COCOATE | 13.50 | 5.00 | 11.50 | 10.90 | 13.50 |
| | EMANON 1112 (HLB = 14) (KAO) | POLYETHYLENGLYCOL MONOLAURATE | | 6.50 | | | |
| | RHEODOL 430V (HLB = 10.5) (KAO) | POLYOXYETHYLENE SORBITOL TETRAOLEATE | 3.00 | 3.00 | 3.00 | 3.50 | 3.00 |
| COMPONENT (B) | COSMOL 41V (HLB = 8) (NISSIN OILIO) | POLYGLYCERYL MONOISOSTEARATE | 2.50 | 4.50 | 4.50 | 4.60 | 2.50 |
| | PARLEAM EX (17 mPa · s) (NOF CORP.) | LIQUID ISOPARAFFIN | | 2.00 | | | 10.00 |
| COMPONENT (C1) | PARLEAM 4 (3 mPa · s) (NOF CORP.) | LIQUID ISOPARAFFIN | 14.50 | | | | |
| | MARUKASOL R (2 mPa · s) (MARUZEN PETROCHEMICAL) | ISODODECANE | | 8.00 | 5.70 | 9.80 | |
| COMPONENT (C2) | EXCEPARL IPM (10 mPa · s) (KAO) | ISOPROPYL MYRISTATE | 2.70 | 10.00 | | | 10.00 |
| COMPONENT (C3) | CETIOL OE (10 mPa · s) (KAO) | DIOCTYL ETHER | 2.80 | | 14.30 | 9.80 | |
| COMPONENT (D) | GLYCERIN (COSMETIC GRADE) (100%) (KAO) | GLYCERIN | 19.00 | 21.00 | 16.10 | 10.00 | 18.00 |
| | SORBITOL #650 (70%) (KAO) | SORBIT SOLUTION | 9.00 | | 8.90 | | 9.00 |
| COMPONENT (E) | 1,3-BUTYLENE GLYCOL-P | 1,3-BUTYLENE GLYCOL | 12.00 | 19.00 | 15.00 | 18.00 | 12.00 |
| COMPONENT (F) | PEMULEN TR-2 (LUBRIZOL) | ACRYLIC ACID-ALKYL METHACRYLATE COPOLYMER | 0.25 | 0.25 | 0.25 | 0.20 | 0.60 |
| | PEMULEN TR-1 (LUBRIZOL) | ACRYLIC ACID-ALKYL METHACRYLATE COPOLYMER | | | | | |
| | ARISTOFLEX AVC (CLARIANT) | (ACRYLOYL DIMETHYLAMMONIUM/VP) COPOLYMER | | | | | |
| COMPONENT (G) | POTASSIUM CHLORIDE | POTASSIUM CHLORIDE | 0.05 | 0.05 | 0.05 | 0.05 | 0.80 |
| | DL-SODIUM MALATE (1/2 HYDRATE) | SODIUM MALATE | | | | | |
| COMPONENT (H) | PURIFIED WATER | PURIFIED WATER | 13.03 | 13.03 | 13.03 | 25.53 | 12.80 |
| | POTASSIUM HYDROXIDE SOLUTION (48%) | POTASSIUM HYDROXIDE SOLUTION | 0.17 | 0.17 | 0.17 | 0.12 | 0.30 |
| | SODIUM HYDROXIDE (48%) | SODIUM HYDROXIDE | | | | | |
| | FRAGRANCE | | | | | | |
| | | | 100.00 | 100.00 | 100.00 | 100.00 | 100.00 |
| B/(A + B) | | | 0.11 | 0.20 | 0.20 | 0.21 | 0.11 |
| F/(A + B) | | | 0.011 | 0.011 | 0.011 | 0.009 | 0.027 |
| D/E | | | 2.11 | 1.11 | 1.49 | 0.56 | 2.03 |
| F/G | | | 1.14 | 1.14 | 1.14 | 1.18 | 0.75 |
| C1/(C2 + C3) | | | 2.64 | 1.00 | 0.40 | 1.00 | 1.00 |
| VISCOSITY (mPa · s) | | | 1193 | 856 | 869 | 574 | 904 |
| VISCOSITY WHEN DILUTED WITH 1.25 TIMES AS MUCH WATER (mPa · s) | | | 1800 | 1260 | 1098 | 730 | 3838 |
| APPEARANCE WHEN DILUTED WITH 1.25 TIMES AS MUCH WATER | | | TRANSLUCENT | TRANSLUCENT | TRANSLUCENT | TRANSLUCENT | TRANSLUCENT |
| CLEANSING-ABILITY (WP MASCARA) | | | A | A | A | B | B |
| APPLICATION-ABILITY | | | A | A | A | A | A |
| SPREADING-ABILITY | | | A | A | A | A | A |
| RINSING-ABILITY | | | B | A | A | A | B |
| CONDITION AT ROOM TEMPERATURE | | | SINGLE LIQUID PHASE | SINGLE LIQUID PHASE | SINGLE LIQUID PHASE | SINGLE LIQUID PHASE | SINGLE LIQUID PHASE |
| STABILITY (50° C.) | | | ○ | ○ | ○ | ○ | ○ |
| STABILITY (40° C.) | | | ○ | ○ | ○ | ○ | ○ |
| STABILITY (25° C.) | | | ○ | ○ | ○ | ○ | ○ |
| STABILITY (5° C.) | | | ○ | ○ | ○ | ○ | ○ |
| STABILITY (−5° C.) | | | ○ | ○ | ○ | ○ | ○ |

According to the results of Table 1 to 4, it was shown that the skin cleansing agent compositions of Examples had enhanced application-ability to skin and improved spreading-ability, and both of higher cleansing-ability and improved rinsing-ability were able to be achieved. It was shown that it could be compatible with high cleansing-ability with improved rinsing-ability.

In addition to above, it was also confirmed that all of the skin cleansing agent compositions of Examples exhibited enhanced cleansing-ability for foundation or water-soluble mascara.

The invention claimed is:

1. A skin cleansing agent composition having an isotropic liquid phase, which is a bicontinuous structure, and comprising:
   (A) 15 to 30 mass % of a nonionic surfactant having hydrophilic-lipophilic balance (HLB) of higher than 9 and equal to or lower than 20;
   (B) 1 to 15 mass % of a nonionic surfactant having HLB of equal to or higher than 5 and equal to or lower than 9;
   (C) 10 to 40 mass % of an oil agent, which comprises (C1) a hydrocarbon oil and at least one of (C2) ester oil, and (C3) an ether oil and exhibits a viscosity at 30 degrees C. of equal to or lower than 30 mPa·s;
   (D) 10 to 40 mass % of a water-soluble solvent having 3 or more of hydroxyl groups in single molecule;
   (E) 10 to 30 mass % of a water-soluble solvent having 1 or 2 hydroxyl group(s) in single molecule;
   (F) 0.05 to 1.0 mass % of a water-soluble polymer comprising (meth)acrylic acid as a configuration unit, an acryloyl methyl taurate-vinylpyrrolidone copolymer, or a combination thereof;
   (G) 0.001 to 2.0 mass % of a water-soluble inorganic salt, an organic salt having 1 to 8 carbon atoms, or a combination thereof; and
   (H) water.

2. The skin cleansing agent composition as set forth in claim 1, wherein a mass ratio of component (B) over the total mass of component (A) and component (B) being ((B)/((A)+(B))) is 0.05 to 0.21.

3. The skin cleansing agent composition as set forth in claim 1, wherein a mass ratio of component (F) over the total mass of component (A) and component (B) being ((F)/((A)+(B))) is 0.001 to 0.06.

4. The skin cleansing agent composition as set forth in claim 1, wherein a mass ratio of component (D) over component (E) being ((D)/(E)) is 0.1 to 2.5.

5. The skin cleansing agent composition as set forth in claim 1, wherein a mass ratio of component (F) over component (G) being ((F)/(G)) is 0.1 to 10.

6. The skin cleansing agent composition as set forth in claim 1, wherein a mass ratio of component (C1) over the total mass of component (C2) and component (C3) being ((C1)/((C2)+(C3))) is 0.3 to 3.

7. The skin cleansing agent composition as set forth in claim 1, wherein a viscosity of said skin cleansing agent composition at 30 degrees C. is 100 to 2,000 mPa·s.

8. The skin cleansing agent composition as set forth in claim 1, wherein a viscosity of diluted skin cleansing agent composition diluted with an amount of water that is 1.25 times the mass of said skin cleansing agent composition is equal to or higher than 100 mPa·s, and the appearance thereof is transparent or translucent.

9. The skin cleansing agent composition as set forth in claim 1, wherein a content of an ionic surfactant is equal to or lower than 0.05 mass %.

10. The skin cleansing agent composition as set forth in claim 1, wherein a content of (H) water is equal to or higher than 5 mass % and equal to or lower than 30 mass %.

11. The skin cleansing agent composition as set forth in claim 1, in which a content of a silicone based surfactant is equal to or lower than 1 mass %.

12. A skin cleansing agent composition, having an isotropic liquid phase, which is a bicontinuous structure, and comprising:
   (A) 17 to 20 mass % of a nonionic surfactant having hydrophilic-lipophilic balance (HLB) of higher than 9 and equal to or lower than 20;
   (B) 2.5 to 5 mass % of a nonionic surfactant having HLB of equal to or higher than 5 and equal to or lower than 9;
   (C) 15 to 30 mass % of and oil agent, which comprises (C1) a hydrocarbon oil and at least one of (C2) ester oil and (C3) an ether oil and exhibits a viscosity at 30 degrees C. of equal to or lower than 30 mPa·s;
   (D) 21 to 30 mass % of a water-soluble solvent having 3 or more of hydroxyl groups in single molecule;
   (E) 11 to 15 mass % of a water-soluble solvent having 1 or 2 hydroxyl group(s) in single molecule;
   (F) 0.1 to 0.5 mass % of a water-soluble polymer comprising (meth)acrylic acid as a configuration unit, an acryloyl methyl taurate-vinylpyrrolidone copolymer, or a combination thereof;
   (G) 0.01 to 1.0 mass % of a water-soluble inorganic salt, an organic salt having 1 to 8 carbon atoms, or a combination thereof; and
   (H) water.

13. A method, comprising coating said skin cleansing agent composition as set forth in claim 1 over skin having makeup thereon to remove a makeup cosmetic composition.

14. A method, comprising coating said skin cleansing agent composition as set forth in claim 1 on a hand having water and coating it over skin having makeup thereon or on skin having water and makeup thereon to remove a makeup cosmetic composition.

15. The skin cleansing agent composition as set forth in claim 1, wherein (G) is a water-soluble inorganic salt.

16. The skin cleansing agent composition as set forth in claim 15, wherein said water-soluble inorganic salt is a salt of an alkali metal or ammonium with an acid selected from the group consisting of hydrochloric acid, sulfuric acid, nitric acid, phosphoric acid, triphosphoric acid, pyrophosphoric acid and carbonic acid.

17. The skin cleansing agent composition as set forth in claim 15, wherein said water-soluble inorganic salt is selected from the group consisting of sodium chloride, potassium chloride, magnesium chloride, sodium sulfate, potassium sulfate, magnesium sulfate, aluminum sulfate, sodium carbonate, and sodium hydrogen carbonate.

18. The skin cleansing agent composition as set forth in claim 1, wherein (G) is a water-soluble organic salt having 1 to 8 carbon atoms.

19. The skin cleansing agent composition as set forth in claim 18, wherein said water-soluble organic salt having 1 to 8 carbon atoms is a salt of an acid with an alkali metal or ammonium wherein the acid is selected from the group consisting of lactic acid, succinic acid, citric acid, tartaric acid, malic acid, maleic acid, and fumaric acid.

20. The skin cleansing agent composition as set forth in claim 18, wherein said water-soluble organic salt having 1 to 8 carbon atoms is selected from the group consisting of monosodium citrate, disodium citrate, trisodium citrate, potassium lactate, ammonium succinate, and potassium malate.

21. The skin cleansing agent composition as set forth in claim 12, wherein (G) is a water-soluble inorganic salt.

22. The skin cleansing agent composition as set forth in claim 21, wherein said water-soluble inorganic salt is a salt of an alkali metal or ammonium with an acid selected from the group consisting of hydrochloric acid, sulfuric acid, nitric acid, phosphoric acid, triphosphoric acid, pyrophosphoric acid and carbonic acid.

23. The skin cleansing agent composition as set forth in claim 21, wherein said water-soluble inorganic salt is selected from the group consisting of sodium chloride, potassium chloride, magnesium chloride, sodium sulfate, potassium sulfate, magnesium sulfate, aluminum sulfate, sodium carbonate, and sodium hydrogen carbonate.

24. The skin cleansing agent composition as set forth in claim 12, wherein (G) is a water-soluble organic salt having 1 to 8 carbon atoms.

25. The skin cleansing agent composition as set forth in claim 24, wherein said water-soluble organic salt having 1 to 8 carbon atoms is a salt of an acid with an alkali metal or ammonium wherein the acid is selected from the group consisting of lactic acid, succinic acid, citric acid, tartaric acid, malic acid, maleic acid, and fumaric acid.

26. The skin cleansing agent composition as set forth in claim 24, wherein said water-soluble organic salt having 1 to 8 carbon atoms is selected from the group consisting of monosodium citrate, disodium citrate, trisodium citrate, potassium lactate, ammonium succinate, and potassium malate.

\* \* \* \* \*